United States Patent [19]

Hultmark et al.

[11] Patent Number: 4,520,016

[45] Date of Patent: May 28, 1985

[54] BACTERIOLYTIC PROTEINS

[75] Inventors: Dan Hultmark, Nacka; Hakan Steiner, Vallenhuna; Torgny Rasmuson, Umeå; Hans G. Boman, Stockholm, all of Sweden

[73] Assignee: KabiGen AB, Stockholm, Sweden

[21] Appl. No.: 404,119

[22] Filed: Aug. 2, 1982

Related U.S. Application Data

[62] Division of Ser. No. 160,393, Jun. 17, 1980, Pat. No. 4,355,104.

[51] Int. Cl.³ .................. A61K 37/02; C12P 21/00; C12P 21/02; C07C 103/52
[52] U.S. Cl. .................. 514/12; 435/68; 435/70; 260/112.5 R
[58] Field of Search .................. 424/177; 260/112.5 R

[56] References Cited

PUBLICATIONS

*Infection and Immunity,* Dec. 1975, pp. 1426–1438, vol. 12, No. 6, Faye, I. et al., "Insect Immunity".

*Primary Examiner*—Blondel Hazel
*Assistant Examiner*—Robin Lyn Teskin
*Attorney, Agent, or Firm*—Gottlieb, Rackman & Reisman

[57] ABSTRACT

A non-lysozyme highly active bacteriolytic protein which is heat stable and has a relatively low molecular weight. The protein may be produced by immunizing an insect against *E. coli* and recovering the protein from the insect. The protein is useful for extracting proteins from genetically engineered bacteria and as a pharmaceutical for inhibiting certain bacteria.

1 Claim, 3 Drawing Figures

BACTERIOLYTIC PROTEINS

This application is a division of application Ser. No. 160,393, filed June 17, 1980, now U.S. Pat. No. 4,355,104.

BACKGROUND OF THE INVENTION

This invention concerns a novel class of bacteriolytic proteins capable of lysing certain gram negative bacteria, the processes for inducing and obtaining this class of proteins from insect hemolymph and the processes for their utilization.

Recent developments in biochemistry have made available recombinant bacteria that synthesize enzymes and other non-bacterial proteins. These genetically engineered bacteria differ from those that hitherto occurred naturally by containing, along with their own genes, at least portions of genes inserted from other organisms which have instructions encoded in their DNA for synthesizing proteins having important biomedical applications. When the animal gene is properly integrated into the bacterial genome, the resulting recombinant bacteria produces the protein specified by the animal gene. Cultures of the recombinant bacteria are easily grown at low cost and hold out the promise of efficiently producing important proteins. Examples of these developments are the manufacture of a precursor of insulin via rat genes inserted into bacteria, the production of human interferon (a potentially useful antiviral protein), and the production of a protein of the shape and size of human growth hormone via a piece of DNA containing the structural information for human growth hormone integrated into bacteria.

The useful proteins produced by such recombinant bacteria are typically trapped within the bacterial protoplasm and it is necessary to remove the cell wall surrounding the bacteria in order to free the useful protein. This has been done in the past by techniques such as sonification, freeze thawing or grinding techniques that physically destroy the bacterial cell wall. These techniques are both time consuming and non-specific and they are likely to interact with and cause denaturation and/or inactivation of the useful proteins.

The present invention provides processes and substances to significantly increase the yields from genetically engineered bacteria by enabling an efficient lysis of the bacterial cell wall. These novel immune proteins constitute a group herein termed P9. The P9 proteins also appear to be useful as pharmacological substances to control certain bacterial infections.

P9 proteins are produced by injecting live bacteria into insect hemolymph and obtaining the P9 proteins from the induced hemolymph in a manner that does not destroy their bacteriolytic activity.

Prior to the present invention the hemolymph of insects were studied in order to determine which substances were responsible for insect anti-bacterial activity, but little was known concerning the molecular basis for insect immunity to bacterial infection. As late as 1968 it was believed that the enzyme lysozyme fully accounted for all the phenomena of natural, acquired and passively acquired humoral immunity in insects. Mohrig, W. & Messner, B. (1968) *Biol. Zentralbe.* 87, 439-70. However, anti-bacterial factors with properties clearly different from those of lysozyme have also been reported. These were described as small, heat stable, acidic molecules of non-protein nature, Stephens, J. M. & Marshall, J. J. (1962) *Can. J. Microbiol.* 8, 719-725; Gingrich, R. E. (1964) *J. Insect Physiol.* 10, 179-94; Hink, W. F. & Briggs, J. D. (1968) *J. Insect Physiol.* 14, 1025-34; as small, basic proteins or co-factors, Knoshita, T. & Inoue, K. (1977) *Infect. Immun.* 16, 32-36; Bakula, M. (1970) *J. Insect Physiol.* 16, 185-197; or as heat sensitive proteins, Natori, S. (1977) *J. Insect Physiol.* 23, 1169-1173.

The P9 proteins of this invention are clearly distinguished from known procaryotic proteins and eucaryotic proteins which are bactericidal for *Escherichia coli*. The only procaryotic proteins known to be bactericidal for *E. coli* are the colicins, Hardy, K. G. (1975) *Bacteriological Reviews* 39, 464–515, of which the only purified colicin which is known to be bacteriolytic is colicin M, Braun et al. (1974) *Antimicrob. Agents Chemother.* 5, 510-33. Colicin M, however, is clearly different from the P9 proteins of the present invention. The basic eucaryotic proteins present in polymorphonuclear leukocytes are bactericidal for *E. coli* but are distinguished from the present invention by their amino acid composition and molecular weight. The subject matter of the invention relates generally to the subject matter of Hultmark et al., *Eur. J. Biochem.* 106, 7-16(1980).

SUMMARY OF THE INVENTION

The present invention concerns the derivation and use of new types of basic and low molecular weight bactericidal proteins termed P9 proteins that kill and lyse bacteria including *E. coli* and certain other gram negative bacteria. The amino acid compositions of two such distinguishable proteins, termed P9A and P9B, are very similar. The molecular weight of the monomer of P9A is believed to be 3564 and that of the dimer of P9B is believed to be within 20% of about 7000. Both P9A and P9B are heat stable, but differ in their amino acid contents of glutamic acid and methionine. A preferred method of deriving these proteins without destroying their effectiveness comprises a novel purification schedule applied to the hemolymph of pupae of the giant silk moth *Hyalophora cecropia* that have been specially treated to induce immunization by producing P9 proteins.

An object of the present invention is to provide new bacteriolytic proteins in highly purified forms and to identify the amino acid sequence of proteins capable of lysing bacteria, e.g., *E. coli* and certain other gram negative bacteria.

Another object of the present invention is to devise a technique for inducing immunities in insect hemolymph and subsequently isolating new bacteriolytic active proteins without destroying their activity.

Another object of the present invention is to provide an improved method for the efficient lysis of recombinant bacteria in order to extract animal protein manufactured by the bacteria.

Still further objects of the present invention will be apparent to the person skilled in the art from the following detailed description.

BRIEF DESCRIPTION OF THE DRAWINGS

FIG. 3 is a graph depicting the effect of heat on the lytic activity of lysozyme and P9 proteins. The filled symbols in the figure indicate a pH of 6.4; the open symbols indicate a pH of 3.2. Activity against *E. coli* is denoted in the figure by triangles; activity against *M luteus* is denoted by squares.

DETAILED DESCRIPTION OF A PREFERRED EMBODIMENT OF THE INVENTION

To cause the appearance of impure bacteriolytic proteins in the hemolymph of *H. cecropia* such pupae are first vaccinated with *Enterobacter cloacae*, strain β12, suspended in saline. After 12–18 hours, bacteriolytic activity will have been created in the hemolymph, which is potent against some bacteria like *E. coli, Micrococcus luteus* or *Bacillus megaterium* but weak against others like *B. cereus* and *B. thuringiensis* and absent against *Proteus vulgaris*. It is preferable to allow the activity to increase during 4–8 days after which the hemolymph may be collected in ice-cooled tubes containing a few crystals of phenylthiourea and processed at 0°–4° C.

The lysis of *E. coli* is believed to be due to at least two very similar small and basic proteins designated P9A and P9B. The P9 proteins are active against gram negative bacteria such as *E. coli* K12 strain D21f2, *E. coli* K12 strain D21, *E. coli* K12 strain D31, *Enterobacter cloacae*, β11, *Pseudomonas aeruginosa*, OT97, and *Serratia marcescens*, Db1108 but not *S. marcescens* Db11. The *E. coli* K12, strain D31 is a penicillin and streptomycin resistant mutant with a defective lipopolysaccharide. *S. marcescens* Db11 is a streptomycin resistant mutant derived from a parental strain, pathologic for Drosophila. *S. marcescens* Db1108 is a spontaneous phage resistant mutant of Db11. The bacterial strains are discussed in Boman, H. G., Nilsson-Faye, I., Paul, K. & Rasmuson, T. (1974) *Infect. Immun.* 10, 136–145; Monner, D. A., Jonsson, S. & Boman, H. G. (1971) *J. Bacteriol.* 107, 420–432; and Boman, H. G. & Monner, D. A. (1975) *J. Bacteriol.* 121, 455–464.

The immunized pupal hemolymph also exhibits an induced activity against *M. luteus*. This is believed to result from an additional non-P9 protein similar to the lysozyme of the wax moth, *Galleria mellonella*. This lysozyme is present as an impurity that cannot be resolved from the P9 proteins by normal chromatographic purification techniques.

Figure 1:
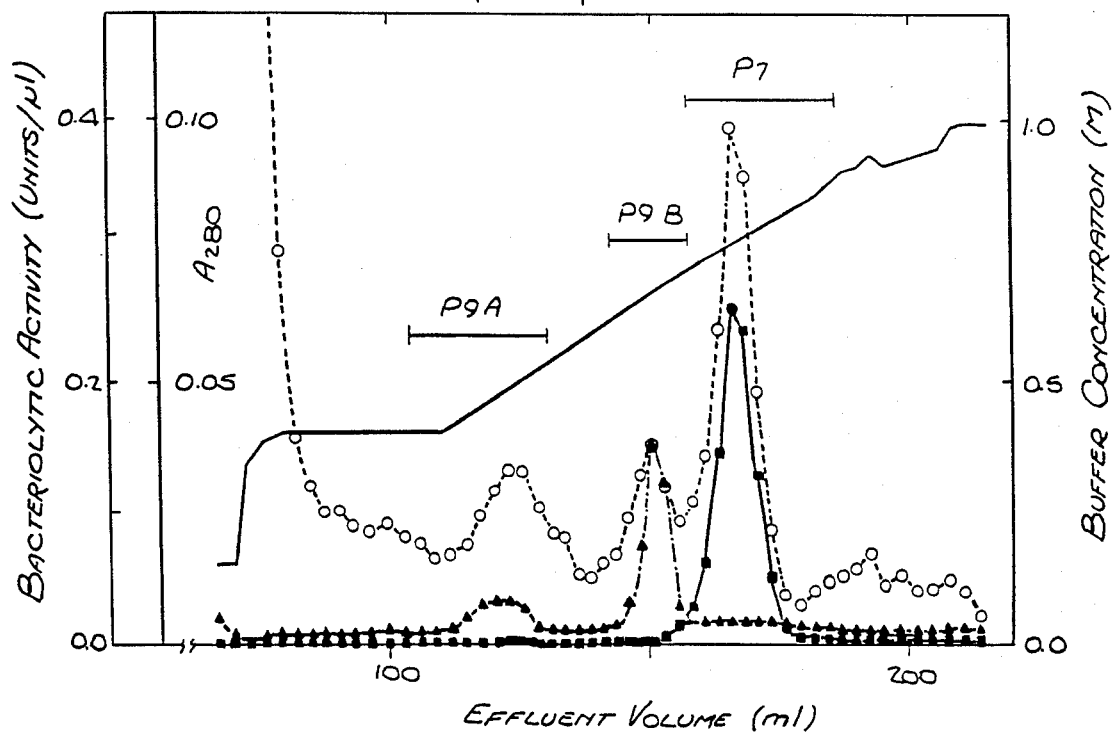
FIG. 1 is a graph depicting the first stage of a chromatographic derivation of P9 proteins from immune hemolymph of *H. cecropia*, and the manner of pooling the active fractions. The solid squares depict bacteriolytic activity against *M. luteus*; the solid triangles depict bacteriolytic activity against *E. coli*; the open circles depict UV absorbance at 280 nm; the solid curve depicts buffer concentration.

A two-stage chromatographic derivation of the P9 proteins without destroying their bacteriolytic activity is performed on a column (size related to load and volumes of gradient 6.5×1.5 cm) of CM-Sepharose (Pharmacia Fine Chemicals, Uppsala, Sweden). In the first stage the column is equilibrated with 0.1M ammonium formate buffer at pH 7.6, containing 0.5% Nonidet P40. The presence of this detergent reduces the adsorption of lipid materials to the column. With large batches of hemolymph (from 40–50 pupae) the flow rate often stops, presumably due to clotting. This problem can be overcome by batchwise adsorption of the basic proteins on CM-Sepharose which is then removed and packed into a column. The column is then washed with 50 ml of the starting buffer and then with 50 ml 0.4M ammonium acetate buffer, pH 5.1, without detergent. The bacteriolytic proteins are then eluted with a linear gradient of 100 ml ammonium acetate buffer from 0.4 to 1.0M, pH 5.1. FIG. 1 shows the manner in which the active fractions are pooled to form the materials separately utilized in the second stage of the chromatographic derivation process. The pooling to form the portion labelled A includes the linear portion of the buffer gradient from about 0.4 to 0.55M; the portion labelled B includes the portion from about 0.60 to 0.75M. The portion labelled P7 includes a lysozyme impurity.

Figure 2:
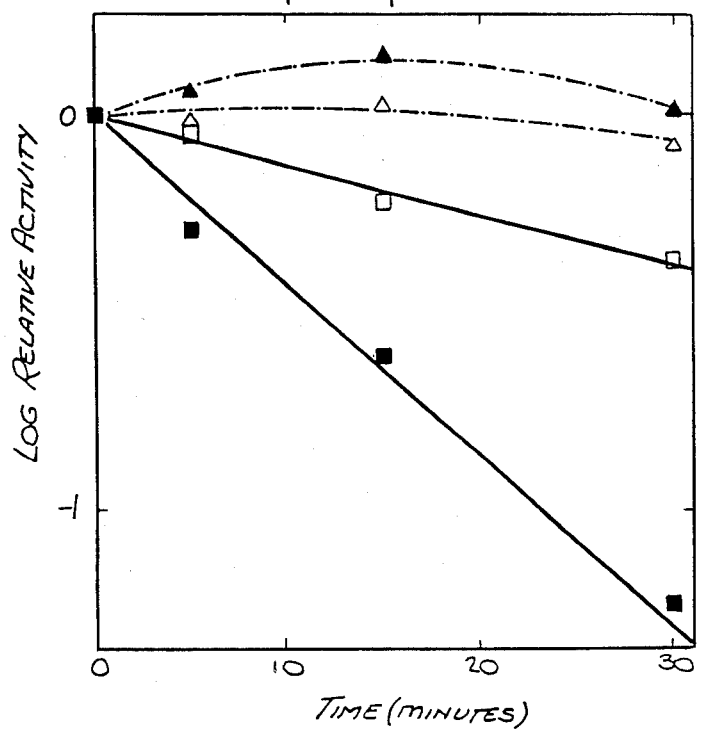
FIG. 2 is a graph depicting the second stage of a chromatographic derivation of P9 proteins and the manner of pooling the active fractions. The solid squares and triangles, open circles and solid curve have the same meaning as in FIG. 1.
Figure 2:
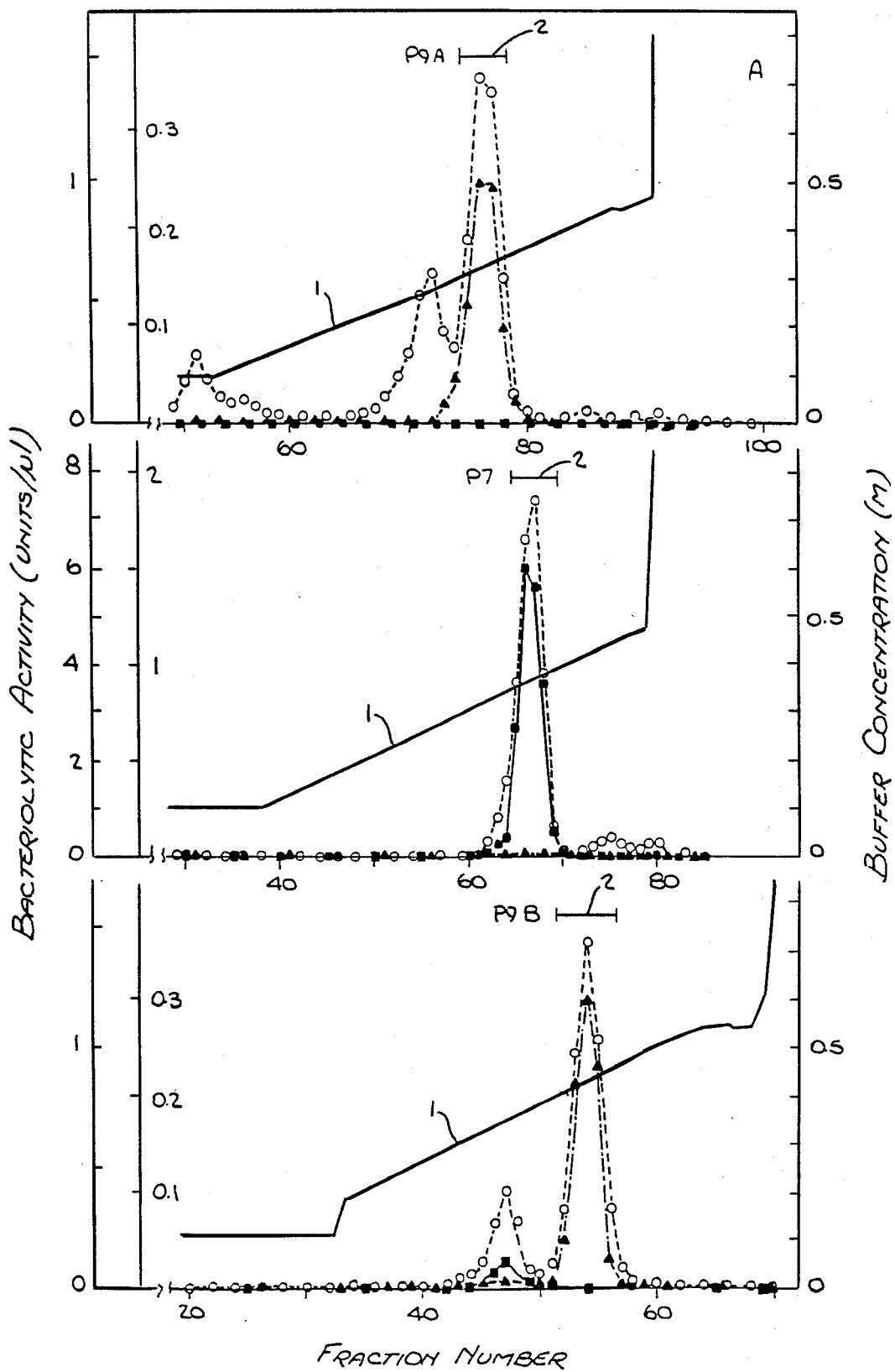

The second chromatographic stage equilibrated at pH 6.6 is performed on the same type adsorbant. The pooled fractions resulting from the first stage are diluted with two volumes of distilled water and separately applied to a second column of CM-Sepharose (17.5×0.5 cm cross linked beaded dextran substituted with carboxymethyl) equilibrated with 0.1M ammonium formate, pH 6.6. The column is first washed with 15 ml of the starting buffer and then eluted with a linear gradient of 40 ml ammonium formate, pH 6.6. Elutions are performed for protein P9A with a 0.1–0.5M gradient of ammonium formate, pH 6.6, and for protein P9B with a higher ionic strength 0.2–0.6M gradient of the same buffer. FIG. 2 shows the linear regions 1 of the buffer gradient and the fractions 2 that were pooled and the manner of pooling the fractions. For P9A the pooled fractions include the range 0.3–0.35M. For P9B the pooled fractions include the range 0.4–0.45M. The alteration of pH affects the elution order and separates the P9 group of proteins into pure forms. The active chromatogram peaks are freeze-dried and dissolved in 0.1M potassium phosphate or 0.15M sodium chloride.

The lytic activity of the P9 proteins against *E. coli* at each stage of the process can be determined turbidimetrically and the total weight of protein measured. For this purpose, one unit of lytic activity is defined as the amount of factor giving 50% reduction of the absorbance of 570 mm (50% lysis) compared to a control. Log phase *E. coli*, strain D31 can be centrifuged and suspended in ice-cold 0.1M phosphate buffer, pH 6.4, to give a density of 30 units on a Klett-Summerson colorimeter ($A_{570}$ 0.3–0.5). A small volume, usually 10 μl, of the sample to be tested is added to 1 ml of bacterial suspension in an ice bath. In the control samples, an equal amount of buffer is substituted. The mixture is incubated (30 minutes at 37° C.) and transferred back to the ice bath during which most of the clearing of the *E. coli* suspension occurs. Results of such a determination, usually measured within 1 h, are tabulated below in Table 1.

TABLE 1

| Fraction | Volume (ml) | Total Protein (mg) | Total Lytic Activity (Units · $10^{-3}$) | Recovery (%) | Specific Lytic Activity (Units/μg of protein) |
|---|---|---|---|---|---|
| Hemolymph | 21.6 | 1220 | 23.4 | 100 | 0.019 |
| Protein P9 A | | | | | |
| Step 1 | 38.4 | 1.2 | 5.2 | 22 | 4.4 |
| Step 2 | 4.15 | — | 2.9 | 18 | — |

TABLE 1-continued

| Fraction | Volume (ml) | Total Protein (mg) | Total Lytic Activity (Units · 10$^{-3}$) | Recovery (%) | Specific Lytic Activity (Units/μg of protein) |
|---|---|---|---|---|---|
| After freeze-drying | 0.56 | 0.33 | 1.9 | 8 | 5.6 |
| Protein P9 B | | | | | |
| Step 1 | 13.6 | 0.95 | 5.2 | 22 | 5.3 |
| Step 2 | 5.45 | — | 3.6 | 15 | — |
| After freeze-drying | 0.57 | 0.46 | 0.88 | 4 | 1.9 |

From these results it can be seen that the specific lytic activity of either protein P9A or B against *E. coli* is demonstrated to be substantially greater than that of the immune hemolymph used as starting material.

The bacteriolytic activity is also plotted in FIGS. 1 and 2 as a function of effluent volume from each chromatographic purification stage.

The molecular weight of the P9 proteins can be determined to within about a 20% error by the method of electrophoresis of denatured protein in SDS (sodium dodecyl sulfate) polyacrylamide gels and more accurately from their amino acid sequence. The amino acid sequence for P9A implies a molecular weight of 3564 daltons. The SDS electrophoresis was carried out at a pH 8.8 in a 20% gel. The mobility of the P9 proteins was compared to that of soybean trypsin inhibitor, horse heart myoglobin, horse heart cytochrome, bovine β-lactoglobulin, hen egg white lysozyme and bovine pancreas insulin to arrive at a value of 7000 daltons which is believed to be the molecular weight of the dimer of P9±20%.

The ultraviolet absorption spectra for P9A has an absorbtivity of 3.0 ml mg$^{-1}$ cm$^{-1}$ at 280 nm (nanometer wavelength). For P9B the absorbtivity is 1.6 ml mg$^{-1}$ cm$^{-1}$.

An analysis was made of the amino acid composition of P9A and P9B. The number of residues was calculated using the molecular weights determined by the SDS-polyacrylamide electrophoresis. The following Table 2 shows the results although it should be understood that the most exact value for the composition of P9A is known from its amino acid sequence which is discussed below.

TABLE 2

| | Immune protein | | | |
|---|---|---|---|---|
| | P9 A | | P9 B | |
| Amino acid | % | residues | % | residues |
|---|---|---|---|---|
| Aspartic acid[a] | 7.9 | (5) | 6.8 | (4-5) |
| Threonine[b] | 3.5 | (2) | 1.6 | (1-2) |
| Serine[b] | 1.7 | (1) | 3.3 | (1-3) |
| Glutamic acid[a] | 11.9 | (7-8) | 6.8 | (4-5) |
| Proline | 3.2 | (2) | 2.8 | (2) |
| Glycine | 11.1 | (7) | 11.9 | (8-9) |
| Alanine | 13.3 | (8-9) | 11.5 | (6-10) |
| Half cystine[c] | 0.0 | (0) | 0.1 | (0) |
| Valine | 8.1 | (5) | 6.3 | (4-5) |
| Methionine | 0.3 | (0) | 3.0 | (2) |
| Isoleucine | 8.7 | (5-6) | 8.3 | (5-6) |
| Leucine | 3.8 | (2) | 4.9 | (3-4) |
| Tyrosine | 0.9 | (0-1) | 0.7 | (0) |
| Phenylalanine | 2.9 | (2) | 3.0 | (2) |
| Lysine | 17.6 | (11-12) | 20.2 | (13-15) |
| Histidine | 0.2 | (0) | 1.2 | (0-2) |
| Arginine | 2.8 | (2) | 5.7 | (3-4) |
| Tryptophan[c] | 2.2 | (1) | 2.0 | (1) |
| Total | | 62-63 | | 67-69 |

[a]Includes the corresponding amide.
[b]Corrected for loss during hydrolysis.
[c]Recoveries are unknown, half cystine is determined after oxidation in air to cystine; values are determined in a single experiment, and should be considered as minimum estimates.

The sequence of amino acids comprising the P9 proteins can also be determined by standard techniques on an automatic amino acid sequenator. They are believed to be the following sequences:

P9A: N-LYS-TRP-LYS-LEU-PHE-LYS-LYS-ILE-GLU-LYS-VAL-GLY-GLN-ASN-ILE-ARG-ASP-GLY-ILE-ILE-LYS-ALA-GLY-PRO-ALA-VAL-ALA-VAL-VAL-GLY-GLN-ALA-THR-C

P9B: N-LYS-TRP-LYS-VAL-(MET)-ILE-(PHE)-LYS-LYS-ILE-(PHE)-GLU-LYS-GLY-ARG-ASN-ILE-(PHE)-ARG-ASN-(LYS)-GLY-

In the sequence for P9B only the N-term sequence is determined. The amino acids in parenthesis represent uncertainties in the immediately preceding amino acid.

TABLE 3

| | Relative Activity | |
|---|---|---|
| Added salt | P9 A | P9 B |
|---|---|---|
| None | 1.0 | 1.0 |
| Sodium sulfate | 0.6 | 1.2 |
| Sodium phosphate | 0.8 | 1.3 |
| Sodium acetate | 0.9 | 4.1 |
| Ammonium formate | 1.3 | 4.5 |

The lytic activity of P9 proteins is substantially influenced by the presence of anions as shown in Table 3, above.

Acetate or formate ions give a four-fold increase in the activity of P9B protein when the ionic strength is maintained at 0.15M with sodium chloride in 0.045M MES-buffer, pH 6.3. The effects of sulfate or phosphate ions are hardly significant. The presence of acetate and formate buffers during the chromatography sequences until their removal by freeze-drying should be taken into account in interpreting the recovery data for protein P9B in Table 1.

The anti-bacterial specificity of P9 proteins was determined for gram negative bacteria. Killing time shown in Table 4 is the time required for killing 90% of the bacteria. Table 4 shows that *E. coli* was highly susceptible to both forms of P9 protein; *E. cloacae* and *P. aeruginosa* were both moderately susceptible while *S. marcescens* Db11 was fully resistant. It is also clear that the heptose-less mutant *E. coli* D21f2 and *S. marcescens* Db1108 both were more sensitive to P9 proteins than their respective parental strains, D21 and Db11.

TABLE 4

| Organism and strain | Bacterial concentration 10⁶ cells/ml | Killing Time P9 A min | P9 B min |
|---|---|---|---|
| *Escherichia coli* K12, D21f2 | 3 | <0.25 | <0.25 |
| *Escherichia coli* K12, D21 | 4 | 0.60 | 1 |
| *Enterobacter cloacae*, 11 | 3 | 12 | 15 |
| *Pseudomonas aeruginosa*, OT97 | 4 | 10 | 5 |
| *Serratia marcescens*, Db1108 | 3 | 48 | 115 |
| *Serratia marcescens*, Db11 | 3 | >120 | >120 |

For *E. coli* D31 the effect of P9 proteins can be observed by simultaneously following the decrease in the absorbance at 570 nm and the viable count of *E. coli*. Eight units of protein P9B per ml in 1 min gave a reduction of viable count from $10^8$ to $<10^5$ while the absorbance dropped 14%.

The mode of action of P9 proteins is not known. It is possible that a single hit of P9 protein is lethal for *E. coli*, while lysis could be either a late stage of a repeated killing reaction or a late step in a sequence of reactions leading to the elimination of bacteria. However, it is not clear if the two forms of P9 protein act catalytically or in a physico-chemical, "detergent-like" fashion.

The heat stability of P9 proteins can be demonstrated by combining samples of protein P9A, protein P9B and lysozyme and incubating them in a boiling water bath. FIG. 3 shows the relative activity as a function of time at pH 6.4 (filled symbols) and 3.2 (open symbols). The activity against *E. coli* (triangles) is compared in FIG. 3 to the activity against *M. luteus* (squares). The former activity is associated with the P9 proteins and the latter with the lysozyme. The heat stability of the P9 proteins is shown to be substantially greater.

A preferred utility of P9 proteins is in connection with the yield of useful proteins from cultures of recombinant *E. coli* bacteria. The use of P9 protein to lyse a broth of *E. coli* that produce human growth hormone yields on the order of 150 mg per liter of broth per 5-hour interval. This represents a 50 to 85% gain in yield over prior methods. This increased efficiency is possibly tied to the fact that the P9 proteins nondestructively disassemble both the outer and the inner membranes of gram negative bacteria.

Another intended use of P9 proteins is as a pharmacological antibiotic for those strains for which it has specific potent effect. In particular, P9 protein is observed to be potent against bacterial strains which are streptomycin and penicillin resistant. In addition, there are no known antibodies for the P9 proteins indicating a wide acceptability for human and veterinary applications. One apparently useful application would be for surface infections because of the high activity against Pseudomonas.

Although certain preferred embodiments of our invention have been described in detail, it should be understood that what we claim as our invention and desire to secure by Letters Patent is described by the following claims.

I claim:

1. A process for inhibiting gram negative bacteria comprising contacting said bacteria with a bactericidally effective amount of a protein selected from the group consisting of P9A and P9B wherein:

(1) P9A comprises the following identifying characteristics:

(a) is capable of lysing *Escherichia coli*;

(b) loses essentially no activity in its action against *E. coli* after heating in boiling water for 30 minutes;

(c) separates from lysozyme by selective elution from a CM Sepharose column using a gradient of ammonium formate buffer;

(d) comprises the first 33 amino acid residues in the following sequence from the N terminal N-LYS-TRP-LYS-LEU-PHE-LYS-LYS-ILE- GLU-LYS-VAL-GLY-GLN-ASN-ILE-ARG-ASP-GLY-ILE-ILE-LYS-ALA-GLY-PRO-ALA-VAL-ALA-VAL-VAL-GLY-GLN-ALA-THR (e) has a monomer molecular weight within 20% of 3564 daltons;

and (2) P9B comprises the following identifying characteristics:

(a) is capable of lysing *Echerichia coli*;

(B) loses essentially no activity in its action against *E. coli* after heating in boiling water for 30 minutes;

(c) separates from lysozyme by selective elution from a CM Sepharose column using a gradient of ammonium formate buffer;

(d) the monomer has the N terminal sequence N-LYS-TRP-LYS-VAL-(MET)-ILE-(PHE)-LYS-LYS-ILE-(PHE)-GLU-LYS-GLY-ARG-ASN-ILE-(PHE)-ARG-ASN-(LYS)-GLY wherein the amino acid residue in parenthesis is an alternative to the immediately preceding amino acid residue;

(c) has a dimer molecular weight within 20% of 7000 daltons.

* * * * *